United States Patent [19]

Shen

[11] 4,228,161

[45] Oct. 14, 1980

[54] ANTI-INFLAMMATORY COMBINATION HAVING REDUCED ULCEROGENICITY

[75] Inventor: Tsung-Ying Shen, Westfield, N.J.

[73] Assignee: Merck & Co., Inc., Rahway, N.J.

[21] Appl. No.: 24,639

[22] Filed: Mar. 28, 1979

[51] Int. Cl.$^2$ .................... A61K 31/405; A61K 31/62
[52] U.S. Cl. ..................................... 424/232; 424/274
[58] Field of Search ................................ 424/274, 232

[56] References Cited

U.S. PATENT DOCUMENTS

| | | | |
|---|---|---|---|
| 3,161,564 | 12/1964 | Morehouse | 424/324 |
| 3,674,870 | 7/1972 | Ruyle | 424/230 |
| 3,714,226 | 1/1973 | Ruyle | 260/473 S |
| 4,016,268 | 4/1977 | Goldenberg | 424/231 |
| 4,066,756 | 1/1978 | Orr et al. | 424/232 |

FOREIGN PATENT DOCUMENTS 1483165  8/1977  United Kingdom .

OTHER PUBLICATIONS

Hanchar et al., Gastroenterology, vol. 72, No. 5, Part 2 (1977).
Robert et al., Prostaglandins, vol. 14, No. 2, pp. 333–338 (1977).
Rainsford, Agents & Actions, vol. 7, 516, pp. 573–577 (1977).
Goburdhum et al., J. Pharma. Methods, vol. 1, pp. 109–114 (1978).
Pauls et al., Science, Jan. 2, 1948, pp. 19–20.
Scrip, Oct. 14, 1973, p. 24.

*Primary Examiner*—Stanley J. Friedman
*Attorney, Agent, or Firm*—Raymond M. Speer; Mario A. Monaco

[57] ABSTRACT

A novel drug combination for more effective treatment of pain, fever, and inflammation with reduced ulcerogenicity comprising (a) 1-(p-chlorobenzoyl)-5-methoxy-2-methylindole-3-acetic acid (indomethacin), and (b) a member selected from phenyl benzoic acid compounds, especially 2-hydroxy-5-(2',4'-difluorophenyl)benzoic acid (diflunisal), wherein the molar ratio of (b) to (a) is from 0.5 to 1.0 to 15.0 to 1.0.

8 Claims, No Drawings

ANTI-INFLAMMATORY COMBINATION HAVING REDUCED ULCEROGENICITY

BACKGROUND OF THE INVENTION

1. Field of the Invention

The present invention relates to a novel drug combination for more effective treatment of pain, fever, and inflammation with reduced ulcerogenicity.

Particularly, the present invention is concerned with the combination of (a) 1-(p-chlorobenzoyl)-5-methoxy-2-methylindole-3-acetic acid (indomethacin), and (b) a member selected from phenyl benzoic acid compounds, especially 2-hydroxy-5-(2',4'-difluoro-phenyl) benzoic acid (diflunisal).

The 1-(p-chlorobenzoyl)-5-methoxy-2-methylindole-3-acetic acid (indomethacin), compound has long been an effective therapeutic agent in the treatment of pain, fever, and inflammation, and has been especially useful in treating rheumatoid arthritis. However, it has long been recognized that use of indomethacin also results in undesirable irritation of the gastrointestinal mucosa, eventually leading, in many cases, to ulceration. All non-steroidal anti-inflammatory agents are also, to a greater or lesser extent, ulcerogenic; and it is hypothesized that a contributing factor to the basic mechanism of gastrointestinal irritation by these agents is the inhibition of prostaglandin production in the gastrointestinal mucosa.

2. Brief Description of the Prior Art

The 1-(p-chlorobenzoyl)-5-methoxy-2-methylindole-3-acetic acid compound employed in the novel drug combination of the present invention is described in U.S. Pat. No. 3,161,654.

The phenyl benzoic acid compounds employed in the novel drug combination of the present invention are described in U.S. Pat. Nos. 3,674,870 and 3,714,226.

The use of various compounds, particulary salicylic acid derivatives, to combat the gastrointestinal ulceration associated with use of various anti-inflammatory drugs, is known. See, for example, (1) Hanchar et al., "Antiulcer Effect of Aspirin", Gastroenterology, Vol. 72, No. 5, Part 2 (1977) which reports the protective effect of aspirin, sodium salicylate, and aminopyrine when used with indomethacin; (2) British Patent No. 1,483,165 which describes anti-flammatory compositions having decreased gastrointestinal side-effects comprising indomethacin or other anti-inflammatory agents together with salicylic acid or an alkali metal salicylate; (3) U.S. Pat. No. 4,016,268 which describes the use of bismuth subsalicylate co-administered with anti-inflammatory drugs to combat gastric ulceration associated with such drugs; (4) Robert and Asano, Prostaglandins, Vol. 14, No. 2, pp. 333–338 (1977) which describes the use of 16, 16-dimethyl $PGE_2$ to prevent intestinal lesions from indomethacin in experimental animals; (5) Japanese Patent Publication No. 5 3062 839 which discloses the use of mepirizole with non-steroidal anti-inflammatory agents to reduce ulcer formation caused by the latter; (6) Rainsford, Agents and Actions, Vol. 7, 516, pp. 573–577 (1977) which discloses that while the mixture of indomethacin and probenecid is effective in reducing the gastric damage by indomethacin, the effect of aspirin and indomethacin is almost additive; (7) Goburdhum et al. J. Pharma. Methods. Vol. 1, pp. 109–114 (1978) which discloses that copper salicylate is more effective than sodium salicylate in achieving inhibition of the ulcerogenic effects of indomethacin; (8) U.S. Pat. No. 4,066,756 which discloses the use of sodium cromoglycate to inhibit the gastrointestinal irritation caused by indomethacin; and (9) Scrip, Oct. 14, 1973, p. 24, which discloses the use of parsalamide or rimazolium methylsulfate to reduce the ulcerogenic potential of indomethacin. However, unlike the majority of co-administered agents described in the prior art, particularly sodium salicylate and aspirin, the phenyl benzoic acid compounds employed in the present invention are, surprisingly, many times more effective on a molar basis.

Gastric ulceration in the rat has also been shown to be inhibited by salicylic acid or aspirin alone. See Pauls et al., Science, Jan. 2, 1948.

SUMMARY OF THE INVENTION

In accordance with the present invention there is provided a novel drug combination for more effective treatment of pain, fever, and inflammation with reduced ulcerogenicity comprising (a) 1-(p-chloro-benzoyl)-5-methoxy-2-methylindole-3-acetic acid (indomethacin), and (b) a member selected from phenyl benzoic acid compounds, especially 2-hydroxy-5-(2',4'-difluorophenyl)benzoic acid (diflunisal), wherein the molar ratio of (b) to (a) is from 0.5 to 1.0 to 15.0 to 1.0, and preferably, from 1.5 to 1.0 to 10.1 to 1.0.

The phenyl benzoic acid compounds employed in the novel drug combination of the present invention to reduce the ulcerogenicity of the indomethacin component of the combination are selected from compounds of the general formula:

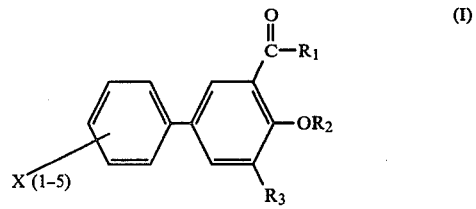

wherein
- X (1–5) is halo, such as fluoro or chloro, but especially fluoro; x being on one or more o the phenyl carbon atoms;
- $R_1$ is selected from the group consisting of hydroxy, phenoxy, diloweralkylamino (such as dimethylamine), diloweralkylamino loweralkoxy (such as diethylaminoethoxy);
- $R_2$ is selected from the group consisting of hydrogen; lower alkanoyl (such as acetyl, propionyl and butyryl); and lower alkoxycarbonyl (such as n-butoxycarbonyl); and
- $R_3$ is selected from the group consisting of hydrogen and methyl.

Also included are the pharmaceutically non-toxic salts of the acids of the compounds of Formula I such as the ammonium, alkali metal (such as sodium or potassium); alkaline earth metals (such as calcium, barium or magnesium); amine; aluminum; iron; choline; glucosamine; S-methyl methonine salts, piperazine, diloweralkylamino lower alkanol, chloroquine and hydroxy chloroquine; the anhydride of said acids, the mixed anhydrides of said acids and 2-acetoxy benzoic acid.

Especially preferred phenyl benzoic acid compounds are those wherein;
$R_1$ is hydroxy, R₂ is hydrogen, R₃ is hydrogen, and X is fluoro, X being on any position of the phenyl moiety when X is one fluoro group, but particularly on the 4'-position; and where X represents two fluoro groups, particularly on the 2' and 4'-positions.

Representative phenyl benzoic acid compounds are as follows:

2-hydroxy-5-(2',4'-difluorophenyl)benzoic acid;
2-acetoxy-5-(2',4'-difluorophenyl)benzoic acid;
2-hydroxy-5-(2'-fluorophenyl)benzoic acid;
2-hydroxy-5-(4'-fluorophenyl)benzoic acid;
2-hydroxy-5-(3'-fluorophenyl)benzoic acid;
2-hydroxy-5-pentafluorophenyl benzoic acid;
2-hydroxy-3-methyl-5-(2',4'-difluorophenyl)benzoic acid;
2-hydroxy-5-(2'-chloro-4'-fluorophenyl)benzoic acid;
N,N-dimethyl-5-(2',4'-difluorophenyl)salicylamide;
β-diethylaminoethyl-5-(2',4'-difluorophenyl)salicylate;
phenyl-5-(2',4'-difluorophenyl)salicylate;
aluminum-2-acetoxy-5-(2',4'-difluorophenyl)-benzoate salt;
aluminum-2-hydroxy-5-(2',4'-difluorophenyl-benzoate salt;
choline-2-acetoxy-5-(2',4'-difluorophenyl)-benzoate salt;
choline-2-hydroxy-5-(2',4'-difluorophenyl)-benzoate salt;
sodium-2-acetoxy-5-(2',4'-difluorophenyl)-benzoate salt
sodium-2-hydroxy-5-(2',4'-difluorophenyl)-benzoate salt;
2-acetoxy-5-(pentafluorophenyl)-benzoic acid;
β-diethylaminoethyl-2-hydroxy-5-(2',4'-difluorophenyl)-benzoate;
β-diethylaminoethyl-2-acetoxy-5-(2',4'-difluorophenyl)-benzoate;
2-(n-butoxycarbonyl)-5-(2',4'-difluorophenyl)salicylate.

The present invention is also concerned broadly with a method of reducing the ulcerogenicity of indomethacin when given perorally to a host to treat pain, fever, and inflammation, comprising co-administering to said host an amount sufficient to reduce the ulcerogenicity of the indomethacin, of a phenyl benzoic acid compound as utilized in the present invention. Such co-administration may simply take the form of simultaneous administration of the indomethacin and phenyl benzoic acid compound, without any requirement that the two compounds be physically combined. More advantageously, however, co-administration will take the form of treatment utilizing a physical mixture of the indomethacin and phenyl benzoic acid compound together with a pharmaceutically acceptable carrier.

The treatment of pain, fever, and inflammation with reduced ulcerogenicity in accordance with the preferred method of the present invention is thus accomplished by orally administering to patients in need of such treatment a composition having as its active ingredient a mixture of indomethacin and a compound of Formula I, in proportional weight amounts such that the molar ratio of the compound of Formula I to the indomethacin is from 0.5 to 1.0 to 15.0 to 1.0, in a non-toxic pharmaceutically acceptable carrier, preferably in tablet or capsule form.

The non-toxic pharmaceutical carrier may be for example, either a solid or a liquid. Exemplary of solid carriers are lactose, corn starch, belatin, talc, stearic acid, magnesium stearate, terra alba, sucrose, agar, pectin, cab-o-sil, acacia. Exemplary of liquid carriers are peanut oil, olive oil, sesame oil and water. Similarly, the carrier or diluent may include a time delay material such as glyceryl monostearate or glyceryl disterate alone or with a wax.

Several pharmaceutical forms of the therapeutically useful compositions can be used. For example, it a solid carrier is used, the compositions may take the form of tablets, capsules, powders, troches or lozenges, prepared by standard pharmaceutical techniques. If a liquid carrier is used, the preparation may be in the form of a soft gelatin capsule, a syrup or a liquid suspension. Particularly desirable are pharmaceutical forms which provided sustained release, such as sustained release capsules, and constant rate delivery, such as tablets coated with a semipermeable membrane where the drug and excipients develop an osmotic pressure which delivers a saturated solution of the drug through an orifice of controlled size at a constant rate. See U.S. Pat. Nos. 3,845,770, and 3,916,899.

The indomethacin and active compounds of Formula I, and of the compositions of this invention are present in an amount sufficient to treat pain, fever, and inflammation, that is, to reduce pain, fever, and inflammation. Advantageously, the composition will contain the active ingredient, namely, the indomethacin and compound of Formula I in an amount of from about 1 mg. to 70 mg. per kg. body weight per day (50 mg. to 5 g. per patient per day), preferably from about 2 mg. to 35 mg. per kg. body weight per day (100 mg. to 2.5 g. per patient per day).

The preferred method of treatment of this invention comprises internally administering to a patient (animal or human), indomethacin and a compound of Formula I, admixed with a non-toxic pharmaceutical carrier such as exemplified above. The mixture of the indomethacin and compound of Formula I will be present in an amount of from 1 mg. to 70 mg./kg. body weight per day, preferably from about 2 mg. to about 35 mg. per kilogram body weight per day and especially from 4 mg. to 20 mg./kg. body weight per day. The most rapid and effective analgesic, anti-pyretic, and anti-inflammatory effect is obtained from oral administration of a daily dosage of from about 4 to 20 mg./kg. day. It should be understood, however, that although preferred dosage ranges are given, the dose level for any particular patient depends upon the activity of the specific compound employed. Also many other factors that modify the actions of drugs will be taken into account by those skilled in the art in the therapeutic use of medicinal agents, for example, age, body weight, sex, time of administration, route of administration, rate of excretion, drug combination, reaction sensitivities and severity of the particular disease.

The more effective treatment of pain, fever, and inflammation with reduced ulcerogenicity achieved with the novel drug combination of the present invention was evaluated in a bioassay designed to measure the reduced ulcerogenicity of the novel drug combination as compared to indomethacin alone. In accordance with the procedures of this bioassay, a total of 10 young adult male Sprague-Dawley rats weighing 125 g. to 175 g. are used for each different treatment group. The animals are marked, weighed, and distributed randomly into groups. All drugs are given in a single dose, suspended in 0.5% methylcellulose using a Virtis—23 homogenizer. The animals are allowed food and water during the test period. After 72 hours the animals are weighed and then sacrificed using carbon dioxide. The abdominal cavity is opened and the entire length of the small intestine is removed. A 20 ml. syringe containing water with a rat dosing needle attached is inserted into the pyloric end of the intestine. The intestine is flushed and the opposite end clamped with a hemostat. The intestine is distended by injecting additional water until the intestinal wall becomes firm. A perforation is indicated by a leak or bursting of the intestinal wall. One perforation or adhesion of two loops of intestine constitutes a positive result. The study is performed blind and the score for a group is recorded as incidence or percent. If a dose-response curve is determined, then the amount of drug required to produce perforations in 50% of the animals can be estimated. The results of the bioassay for the combination of diflunisal and indomethacin on a 4:1 weight ratio basis are illustrated in the table of values below.

TABLE I

| Dose of indomethacin (mg./kg.) | Percent of Rats with Perforations | |
|---|---|---|
| | Indomethacin alone | Indomethacin + Diflunisal (1:4) |
| 6.7 | 50 | 10 |
| 8.0 | 90 | 0 |
| 9.6 | 100 | 0 |
| 11.5 | 100 | 80 |

The above data clearly shows that diflunisal, on a 4:1 weight basis, has the ability to dramatically reduce the ulcerogenicity of indomethacin.

The bioassay described above was employed to compare the effectiveness of the phenyl benzoic acid compounds employed in the novel drug combination of the present invention is reducing the ulcerogenicity of indomethacin with sodium salicylate and aspirin (acetyl-salicylic acid). The results of the bioassay are illustrated in TABLE II below.

TABLE II

| Indomethacin Dose(mg./kg.) | Protective Agent | Dose (mg./kg.) | Approximate Molar Ratio | Percent of Rats with Perforations |
|---|---|---|---|---|
| 8.0 | None (Vehicle) None | — | — | 100 |
| 9.6 | (Vehicle) | — | — | 100 |
| 8.0 | Diflunisal | 5.6 | 1 | 80 |
| 9.6 | " | 6.7 | 1 | 80 |
| 8.0 | " | 11.2 | 2 | 60 |
| 9.6 | " | 13.4 | 2 | 60 |
| 8.0 | " | 22.4 | 4 | 0 |
| 9.6 | " | 26.8 | 4 | 0 |
| 8.0 | None (Vehicle) None | — | — | 100 |
| 9.6 | (Vehicle) | — | — | 100 |
| 8.0 | Aspirin | 32.0 | 8 | 80 |
| 9.6 | " | 38.4 | 8 | 80 |
| 8.0 | " | 64.0 | 16 | 20 |
| 9.6 | " | 76.8 | 16 | 60 |
| 8.0 | " | 128.0 | 32 | 20 |

TABLE II-continued

| Indomethacin Dose(mg./kg.) | Protective Agent | Dose (mg./kg.) | Approximate Molar Ratio | Percent of Rats with Perforations |
|---|---|---|---|---|
| 9.6 | " | 153.6 | 32 | 20 |
| 8.0 | None (Vehicle) None | — | — | 100 |
| 9.6 | (Vehicle) | — | — | 100 |
| 8.0 | Sodium Salicylate | 16.0 | 4.5 | 80 |
| 9.6 | Sodium Salicylate | 19.2 | 4.5 | 100 |
| 8.0 | Sodium Salicylate | 32.0 | 9 | 80 |
| 9.6 | Sodium Salicylate | 38.4 | 9 | 80 |
| 8.0 | Sodium Salicylate | 64.0 | 18 | 20 |
| 9.6 | Salicylate | 76.8 | 18 | 40 |

The data in the above table clearly demonstrates the surprisingly greater effectiveness of the phenyl benzoic acid compounds employed in the novel drug combination of the present invention in reducing the ulcerogenicity of indomethacin, as compared to aspirin and sodium salicylate.

Another bioassay was designed to measure the reduced ulcerogenicity of the novel drug combination of the present invention. This bioassay was intended to observe the acute effects of various treatments on the gastric mucosa. In accordance with the procedures of this bioassay, a total of 22 young adult male Sprague-Dawley rats of a particular offspring available from Camm Research of New Jersey, weighing between 120 g. and 200 g. are used for each different treatment group, including controls. The animals are marked, weighed, and distributed randomly into groups and the bioassay is done blind. The rats are fasted for at least 24 hours and then given 20 mg./kg. of indomethacin, suspended in 0.5% methylcellulose, a dose known to produce gastric lesions within 4 hours. The control animals receive no additional treatment, while the test animals receive various dosages of the protective compounds together with the indomethacin. All drugs, including the combinations, are given in a single dose, suspended in 0.5% methylcellulose using a Virtis −23 homogenizer. The animals are not allowed food and water during the test period. After 4 hours the animals are weighed and then sacrificed using carbon dioxide. The stomach is exposed, excised, and opened along its lesser curvature, and then washed gently with saline. The surface of the gastric mucosa is then examined for bloody lesions equal to or greater than 2 millimeters in diameter, and these, if present, are counted. If the number of such lesions exceeds 10, it is recorded as 10. In addition to counting the number of lesions, a record is kept of the number of animals free of lesions. The results of the bioassay are illustrated in TABLE III below.

TABLE III

| Indomethacin Dose (mg./kg.) | Protective Agent | Dose (mg./kg.) | Approximate Molar Ratio | Gastric Lesions | | |
|---|---|---|---|---|---|---|
| | | | | Total Number | % Change from Control | Number and % of Rats Having Lesions |
| 20 | None (Vehicle) | — | — | 131 | — | $\frac{21}{22}$ 95 |
| 20 | Diflunisal | 28 | 2 | 119 | −9.2 | 22 100 |

TABLE III-continued

| Indomethacin Dose (mg./kg.) | Protective Agent | Dose (mg./kg.) | Approximate Molar Ratio | Gastric Lesions | | Number and % of Rats Having Lesions | |
|---|---|---|---|---|---|---|---|
| | | | | Total Number | % Change from Control | | |
| 20 | Diflunisal | 56 | 4 | 57 | −56.5 | 18/22 | 82 |
| 20 | Diflunisal | 112 | 8 | 25 | −80.9 | 6/22 | 27 |
| 20 | Sodium Salicylate | 36 | 4 | 99 | −24.4 | 22/22 | 100 |
| 20 | Sodium Salicylate | 72 | 8 | 90 | −31.3 | 18/22 | 86 |
| 20 | Sodium Salicylate | 144 | 16 | 45 | −65.5 | 11/22 | 50 |

EXAMPLE

| Ingredient | Amount |
|---|---|
| Indomethacin | 8.03 kg. |
| Diflunisal | 45.00 kg. |
| Hydroxypropyl cellulose | 1.53 kg. |
| Pregelatinized starch | 19.90 kg. |
| Microcrystalline cellulose | 7.83 kg. |
| Magnesium stearate | 0.72 kg. |

The following procedure produces 255 mg. film-coated compressed tablets containing 140 mg. of diflunisal and 25 mg. of indomethacin, an 8:1 molar ratio.

To 22.5 l. of ethanol is added 1.53 kg. of hydroxypropyl cellulose, mixed until dissolved, and then held aside. To a mixer is added 45.00 kg. of diflunisal and the hydroxypropyl cellulose solution is than added with mixing. There is then added 19.90 kg. of pregelatinized starch, 7.83 kg. of microcrystalline cellulose, and a solution of 153.5 l. of water and 4.5 l. of ethanol mixed together. The total mixture is milled and dried, and then milled again. To the dry mixture there is next added 8.03 kg. of indomethacin with mixing, and then 0.72 kg. of magnesium stearate. After final mixing, the preparation is compressed into tablets weighing 255 mg. These tablets are then film coated with a composition prepared from hydroxypropylmethyl cellulose, hydroxypropyl cellulose, talc, and titanium dioxide to form a white film coated tablet.

What is claimed is:

1. In combination:
   (a) 1-(p-chlorobenzoyl)-5-methoxy-2-methylindole-3-acetic acid; and
   (b) a member selected from phenyl benzoic acid compounds of the formula:

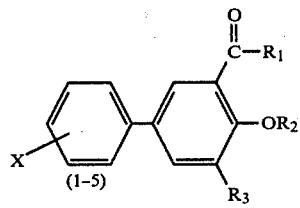

wherein
$X_{(1-5)}$ is halo; X being on one or more of the phenyl carbon atoms;

$R_1$ is selected from the group consisting of hydroxy, phenoxy, diloweralkylamino, and diloweralkylamino loweralkoxy;

$R_2$ is selected from the group consisting of hydrogen; lower alkanoyl; and lower alkoxycarbonyl; and $R_3$ is selected from the group consisting of hydrogen and methyl; and pharmaceutically acceptable, non-toxic salt thereof; wherein the molar ration of (b) to (a) is from 0.5 to 1.0 to 15.0 to 1.0.

2. The combination of claim 1 wherein the phenyl benzoic acid compound is 2-hydroxy-5-(2',4'-difluorophenyl) benzoic acid.

3. A method of treating pain, fever, and inflammation which comprises orally administering to a patient in need of such treatment, daily doses of from 1 mg. to mg./kg. of body weight of the combination of
   (a) 1-(p-chlorobenzoyl)-5-methoxy-2-methylindole-3-acetic acid; and
   (b) a member selected from phenyl benzoic acid compounds of the formula:

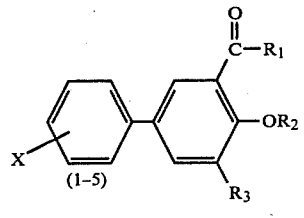

wherein
$X_{(1-5)}$ is halo; X being on one or more of the phenyl carbon atoms;

$R_1$ is selected from the group consisting of hydroxy, phenoxy, diloweralkylamino, and diloweralkylamino loweralkoxy;

$R_2$ is selected from the group consisting of hydrogen; lower alkanoyl; and lower alkoxycarbonyl; and $R_3$ is selected from the group consisting of hydrogen and methyl;

and pharmaceutically acceptable, non-toxic salt thereof; wherein the molar ratio of (b) to (a) is from 0.5 to 1.0 to 15.0 to 1.0.

4. The method of claim 3 wherein the phenyl benzoic acid compound is 2-hydroxy-5-(2',4'-difluorophenyl) benzoic acid.

5. A pharmaceutical composition for treating pain, fever, and inflammation consisting of a non-toxic pharmaceutical carrier and an effective amount of the combination of (a) 1-(p-chlorobenzoyl)-5-methoxy-2-methylindole-3-acetic acid; and
(b) a member selected from phenyl benzoic acid compounds of the formula:

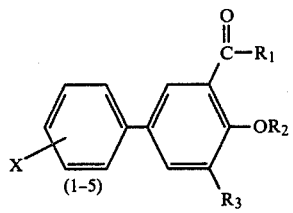

wherein
$X_{(1-5)}$ is halo; X being on one or more of the phenyl carbon atoms;
$R_1$ is selected from the group consisting of hydroxy, phenoxy, diloweralkylamino, and diloweralkylamino loweralkoxy;
$R_2$ is selected from the group consisting of hydrogen; lower alkanoyl; and lower alkoxycarbonyl; and
$R_3$ is selected from the group consisting of hydrogen and methyl; and pharmaceutically acceptable, non-toxic salt thereof; wherein the molar ratio of (b) to (a) is from 0.5 to 1.0 to 15.0 to 1.0.

6. The composition of claim 5 wherein the phenyl benzoic acid compound is 2-hydroxy-5-(2',4'-difluorophenyl)benzoic acid.

7. A method of reducing the ulcerogenicity of 1-(p-chlorobenzoyl)-5-methoxy-2-methylindole-3-acetic acid when given perorally to a host to treat pain, fever, and inflammation, comprising co-administering to said host an amount sufficient to reduce the ulcerogenicity of said 1-(p-chlorobenzoyl)-5-methoxy-2-methylindole-3-acetic acid, of a member selected from phenyl benzoic acid compounds of the formula:

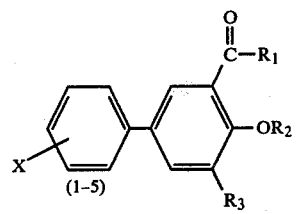

wherein
$X_{(1-5)}$ is halo; X being on one or more of the phenyl carbon atoms;
$R_1$ is selected from the group consisting of hydroxy, phenoxy, diloweralkylamino, and diloweralkylamino loweralkoxy;
$R_2$ is selected from the group consisting of hydrogen; lower alkanoyl; and lower alkoxycarbonyl; and
$R_3$ is selected from the group consisting of hydrogen and methyl; and pharmaceutically acceptable, non-toxic salt thereof.

8. The method of claim 7 wherein the phenyl benzoic acid compound is 2-hydroxy-5-(2',4'-difluorophenyl) benzoic acid.

* * * * *